United States Patent [19]
Guidotti et al.

[11] Patent Number: 5,022,765
[45] Date of Patent: Jun. 11, 1991

[54] NULLING OPTICAL BRIDGE FOR CONTACTLESS MEASUREMENT OF CHANGES IN REFLECTIVITY AND/OR TRANSMISSIVITY

[75] Inventors: Daniel Guidotti, Yorktown Heights; Swie-in Tan, Stormville; John G. Wilman, Hopewell Junction, all of N.Y.

[73] Assignee: International Business Machines Corporation, Armonk, N.Y.

[21] Appl. No.: 112,803

[22] Filed: Oct. 23, 1987

[51] Int. Cl.$^5$ .............................................. G01J 4/00
[52] U.S. Cl. .................................. 356/435; 356/370; 356/445
[58] Field of Search .................. 356/322, 364–369, 356/370, 435, 445, 447–448; 250/225; 374/120, 161, 162

[56] References Cited

U.S. PATENT DOCUMENTS

| | | | |
|---|---|---|---|
| 2,126,410 | 8/1938 | Pineo | 250/225 |
| 2,430,833 | 11/1947 | Stearns et al. | 356/369 |
| 2,792,484 | 5/1957 | Gurewitsch et al. | 374/161 |
| 3,489,906 | 1/1970 | Beer | 356/435 |
| 3,518,003 | 6/1970 | Meyn | 356/435 |

FOREIGN PATENT DOCUMENTS 375478  5/1973  U.S.S.R. ............................. 356/445

*Primary Examiner*—Richard A. Rosenberger
*Attorney, Agent, or Firm*—Alexander Tognino; Philip J. Feig

[57] ABSTRACT

A nulling optical bridge is disclosed herein for the measurement of the difference in the relative power of more than one light beam. The bridge can be used to precisely measure the change in reflectivity and/or transmissivity of a semiconductor device or metal. The bridge operates by splitting at least one illumination source into a number of beams wherein one of said beams is made to traverse the sample whose change in transmissivity and reflection characteristics is to be measured. A rotating polarizer is used to equate the intensity of the variable and nonvariable beams under feedback servo control from a photodetector. The incremental quantity of rotation of the polarizer can be calibrated to correspond to a number of characteristics of the sample.

11 Claims, 3 Drawing Sheets

# NULLING OPTICAL BRIDGE FOR CONTACTLESS MEASUREMENT OF CHANGES IN REFLECTIVITY AND/OR TRANSMISSIVITY

BACKGROUND OF THE INVENTION

1. Field of the Invention

This invention relates to a nulling optical bridge device and more specifically to a nulling optical bridge device which measures changes in reflectivity and/or transmissivity as a function of change in the relative power of two light beams.

2. Description of Related Art

It is necessary, for process characterization and control, to measure the characteristics of a semiconductor device, during various stages of processing.

For measuring temperature, contactless temperature monitoring is often the preferred method for taking these types of measurements. Contactless temperature measurement is, typically, accomplished by calibrated monitoring of the black-body radiation of the device (see for example U.S. Pat. Nos. 3,442,678; 3,462,224; 3,611,806; 3,654,809; 3,771,874; 4,020,095; 4,498,765). While this is a generally accepted method, it is not applicable under all conditions and is insensitive and subject to inaccuracies and error as for example when sample emissivity changes as a function of temperature or processing, or when emissivity is non-uniform over the sample surface or unknown, as when applied to silicon samples at temperatures of 500° C. or less.

As a general scientific principle, it is known that a change of temperature in many substances, such as semiconductors and metals, is accompanied by a change in the optical reflectivity $\Delta R$ and/or transmissivity of that substance. In addition, it is also recognized that the relative change in a sample's temperature $\Delta T=(T-T_o)$ with respect to some reference temperature $T_o$ (e.g., room temperature) can be determined by measuring the relative change in the optical reflectivity $\Delta R=R(T)-R(T_o)$ and/or transmissivity of that sample. However, these principles have, heretofore, been unable to be applied to contactless temperature measurement of devices comprised of a variety of materials, as the fractional change in reflectivity $\Delta R/R$ and/or transmissivity with temperature for many of these materials is too small to be accurately measured. For example, for silicon at temperatures less than about 500° C., $\Delta R/R(T) \simeq 5 \times 10^{-5}$ for a change in temperature of 1° C. The accuracy of temperature measurements at these small changes becomes increasingly unreliable, as conventional light sources used for such measurements (for example, small lasers and/or incandescent lights) are subject to power variations in the range of 0.1-1.0%. These power variations make it impossible to obtain repeatable temperature resolution to the needed accuracy of about 0.1° C. over a range of several hundred degrees centigrade.

One such device for the contactless measurement of temperature is shown in IBM Technical Disclosure Bulletin, Volume 28, No. 9, pp. 4004-4005, 1986, "In Situ, Contactless and Non-Destructive Measurement of the Temperature Variation Over the Surface of a Silicon Wafer" by D. Guidotti, S. I. Tan (inventors herein) and J. A. Van Vechten. However, the precision of the measurements made by this device are severely limited by the well recognized power fluctuation of the laser. These power fluctuations are known to introduce large noise components into the temperature measurement making the device unable to be used in applications requiring accurate temperature measurements.

It is therefore an object of the present invention to develop a device for the contactless measurement of changes in reflectivity and/or transmissivity of a material under processing.

It is therefore a further object of the present invention to develop a device for the contactless measurement of temperature of the material under processing with an accuracy of about 0.1° C. over several hundred degrees ° C.

It is a still further object of the present invention to develop a device for the contactless measurement of ion implantation dose of a material under processing.

SUMMARY OF THE INVENTION

With the subject invention an accurate, null-point technique for measuring the difference in the relative power of two light beams has been developed which allows one to make a very accurate determination of the change in reflectivity and/or transmissivity of a sample, irrespective of source power fluctuations. By measurement of this change in reflectivity ($\Delta R$) or transmissivity as caused: by a change in the sample's temperature ($\Delta T$) with respect to a known temperature ($T_o$) or by ion implantation dose, one is able to accurately measure either of these parameters of the sample without contact.

The basics of this measurement technique are as follows. An incident optical beam is polarized so that the electric field direction makes an angle ($\phi$) of about 45° with respect to some optic axis of a polarization sensitive beamsplitter prism. The light emerging from the polarization sensitive beamsplitter prism is split into two orthogonally polarized beams (A and B) of nearly equal power, which diverge at some angle ($\theta$) determined by the characteristics of the polarization sensitive beamsplitter prism. A Rochon prism or other suitable optical element can be used as a polarization sensitive beamsplitter prism. One beam (A) is directed into a photodetector (PDA) while the other beam (B) is reflected or transmitted by the sample and is incident on a second photodetector (PDB). The photo-current from detectors PDA and PDB is proportional to the power in beams A and B, respectively. The difference signal (A−B) is amplified and measured.

Inaccuracies from power fluctuations in the light source are completely solved by using a null-point measurement of the difference signal (A−B). This is accomplished by rotating the polarizer by some angle $\Delta\phi$ in order to actively maintain the null condition (A−B)=0 at all times. For example, a change in sample temperature $\Delta T$ will cause the sample reflectivity or transmissivity (and therefore the power in beam B) to vary. The direction of the electric field of the incident optical beam is then rotated, as with a polarizer, by an angle ($\Delta\phi$) with respect to some optic axis of the polarization sensitive beamsplitter prism, so as to restore the null condition (A−B)=0 which makes this measurement independent of power fluctuations of the light source. When the change in polarization angle $\Delta\phi$ is small, the resulting change in said polarization angle $\Delta\phi$ is linearly proportional to $\Delta T$ to a high degree of accuracy.

To measure the change in sample temperature, or ion implantation dose as stated, the polarization direction of the incident optical beam is rotated with respect to an optic axis of the polarization sensitive beamsplitter until beams A and B are made to have equal power at some initial dose or reference temperature $T_o$. Now, as the sample temperature or ion implantation dose changes, the polarization orientation $\phi$ is adjusted so as to maintain the null condition $(A-B)=0$. The change in polarization orientation $\Delta\phi$ is then calibrated so as to be translated into a measurement of a change in the sample temperature or ion implantation dose.

The foregoing and other objects, features and advantages of the invention will be apparent from the following more particular description of the invention as illustrated in the accompanying drawings.

DETAILED DESCRIPTION OF THE INVENTION

In order to better appreciate the workings of the subject invention, a brief derivation of the mathematical principles underlying the operation of the device as it relates to the measurement of changes in temperature will be presented.

The optical reflectivity (R) of metals and semiconductors and, equivalently, the optical transmissivity of semiconductors generally depends on sample temperature (T) and the wavelength of the incident light. The following formulation will be described in terms of sample reflectivity, but it should be appreciated by those skilled in that art that the scope and content of the invention encompasses the transmissivity of the sample as well.

At a fixed wavelength, the sample reflectivity can be represented in Taylor series expansion in temperature (T) as:

$$R(T) = R(T_o) + C_1(T - T_o) + \frac{C_2}{2}(T - T_o)^2 + \ldots$$

where $C_1 = dR/dT/T_o$ and $C_2 = d^2R/dT^2T_o$, and $T_o$ is a reference temperature (e.g., room temperature). The coefficients $C_1$ and $C_2$ are generally a function of optical wavelength. At temperatures of 500° C. or less, and at a fixed incident wavelength, these two coefficients are sufficient to characterize the temperature behavior of R (T) for most metals and semiconductors. In the particular case of silicon, only the linear (first power) term in the equation above need be considered when T is less than 500° C., since $C_1$ is known in the literature to have a value in the range $(2-6) \times 10^{-5}$° C.$^{-1}$. Therefore, the temperature of a silicon wafer, relative to some known temperature $T_o$, can be measured by accurately measuring $\Delta R$ as $R(T) - R(T_o) = C_1(T - T_o)$ wherefore $\Delta R = C_1(T - T_o)$. The limitation in the prior art with this approach is that the temperature coefficient of the reflectivity, $C_1$, is small and when conventional light sources, such as, small lasers and incandescent lamps are to be used in such a measuring device, they are subject to power fluctuations in the range 0.1–1.0%. This prevents making the measurement of temperature of a silicon wafer with an uncertainty of less than 1° C.

In the subject invention an accurate, null-point optical bridge for measuring the differences in the relative power of two light beams has been developed. This allows a very accurate determination of the change in reflectivity and/or transmissivity of a sample independent of source power fluctuations. When the change in reflectivity and/or transmissivity is caused by a change in sample temperature or ion implantation dose, the temperature difference or ion implantation dose can be accurately measured.

Figure 1:
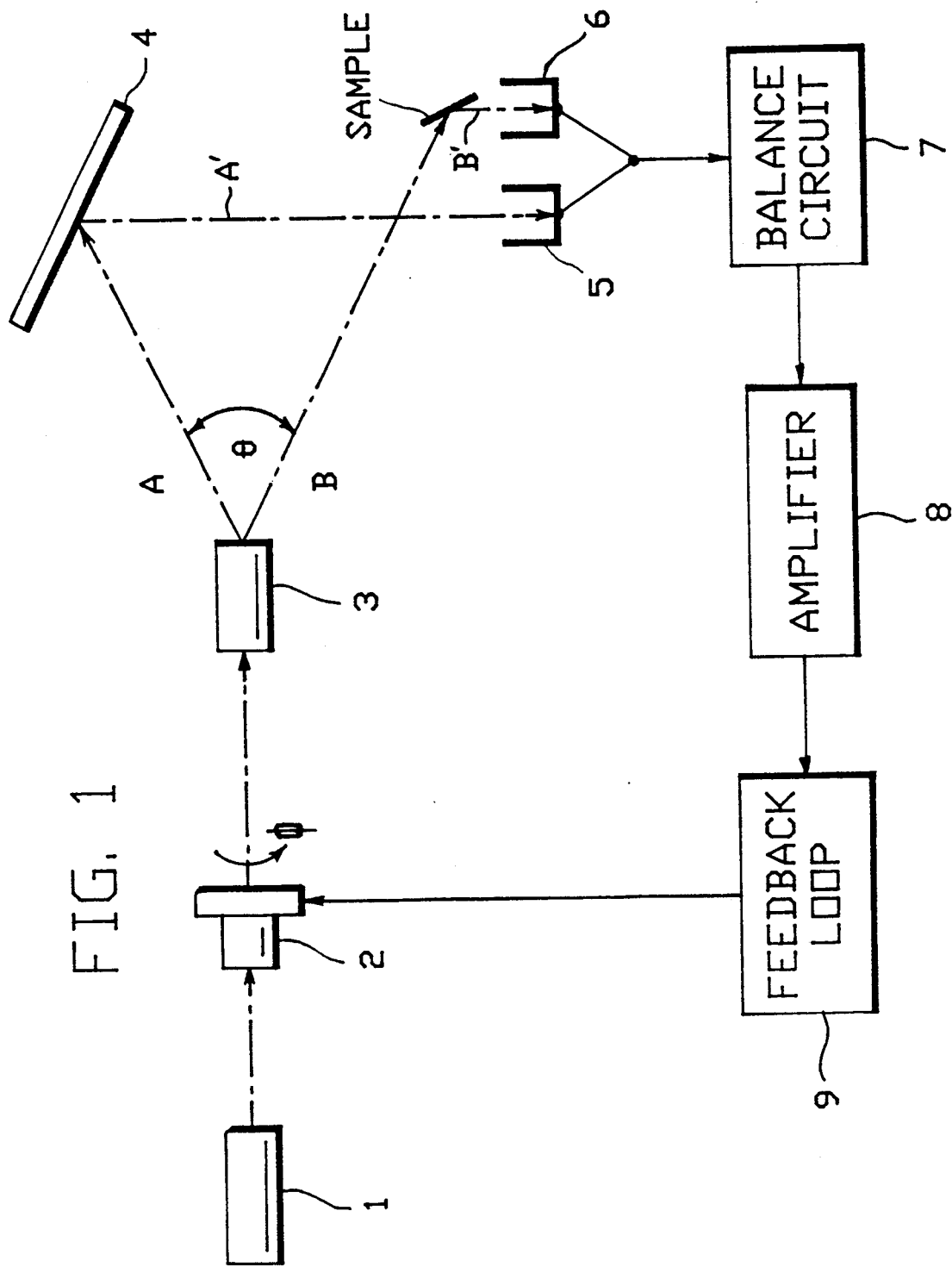
FIG. 1 is schematic arrangement of a nulling optical bridge for the measurement of temperature or ion implantation dose.

Referring now to FIG. 1, the principle of the null-point optical bridge is shown. An optical beam source 1 is linearly polarized by a polarizer 2 such that the electric field direction of the emerging beam makes an angle $(\phi)$ with respect to an optic axis of a polarization sensitive beamsplitter prism 3. A Rochon or nicol prism, or any appropriately cut quartz or calcite crystal can be used for prism 3. The polarization sensitive beamsplitter prism 3 splits the incident light into two orthogonally polarized beams, A and B (the ordinary and extra-ordinary rays), whose relative power depends on the angle $\phi$, and whose divergence angle $(\theta)$ depends on the design properties of prism 3. As $\phi$ is varied by rotating polarizer 2, the difference in power between the two beams $(A-B)$ is varied while the total power emerging from the prism 3 remains constant. The polarizer-prism combination is therefore used as a continuously variable beamsplitter. From prism 3, beam (A) is directed to a reflector 4 and the reflected beam (A') is directed to a photodetector (5). The other beam (B) is directed to the sample to be measured and the reflected beam (B') is reflected from the sample surface at near-normal incidence and is directed into a photodetector (6). The photo-current from detectors 5 or 6 is proportional to the power in beams A' or B', respectively. The photo-current from detectors 5 and 6 is fed to a balance circuit 7 where a difference signal (A'−B') is amplified 8 and measured.

The problem of power fluctuations in the light source is completely eliminated by the null-point measurement of the difference signal (A'−B') which converts a measurement of change in reflectivity or transmissivity into a measurement of the angle $\Delta\phi$. This is done by rotating the polarizer by some angle $\Delta\phi$ so as to maintain the null condition (A'−B') at all times. The null condition renders the device measurement independent of source power fluctuations because whatever the source variation, variations in A and B are identical in magnitude, and occur in synchronism and therefore are always subtracted. The null condition is automatically maintained at all times during a measurement by a feedback loop 9 which governs the rotation of P as dictated by the sign and magnitude of the error signal (A'−B').

The position of the polarizer 2 is adjustable, or instance, by means of a motor rotating the polarizer responsive to the feedback loop 9. The motor may be a stepper motor or preferably a stepper motor calibrated to correspond to the calibrated change in the reflection and/or transmissivity or temperature of the sample.

For example, if a change in sample temperature $\Delta T$ causes a change in sample reflectivity $\Delta R$, then the reflected power in beam A' will vary, and the difference (A'−B') will deviate from null. The polarizer angle $\phi$ is then rotated by an amount $\Delta\phi$ necessary to restore null.

The quantity $\Delta\phi$ is proportional to $\Delta T$ for small angular variations. For silicon, a change in temperature of 1° C. requires an angular rotation of polarizer 2 by an angle of $\Delta\phi \sim 3.85$ arc seconds to restore null, and a linear relationship between $\Delta\phi$ and $\Delta T$ remains a valid approximation at all temperatures of interest up to the melting point of silicon.

The variation of sample reflectivity and/or transmissivity with temperature forms part of the physical basis for the contactless temperature measurement, while the null-point optical bridge is a design configuration which allows for a high degree of sensitivity.

Figure 2:
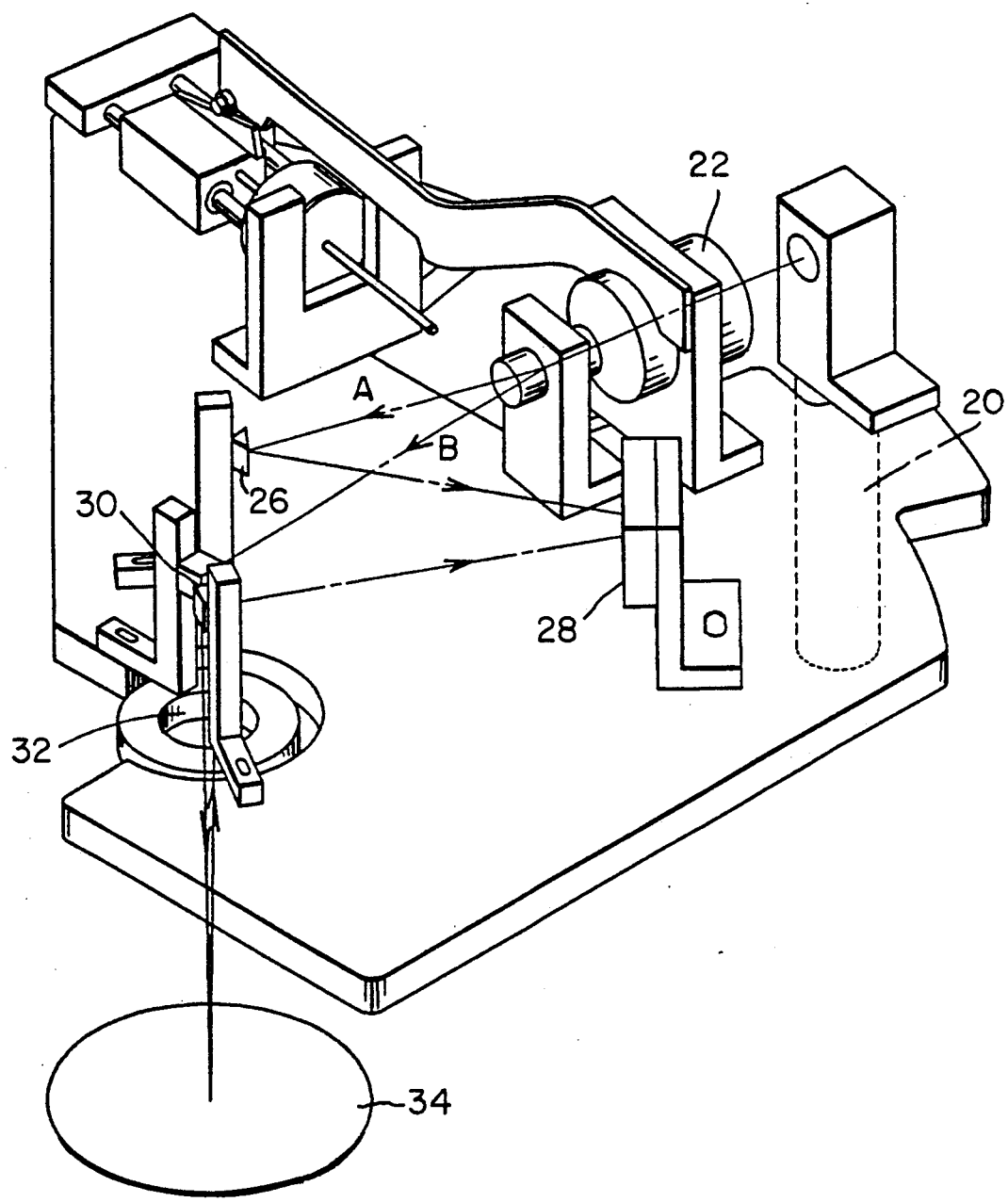
FIG. 2 is an isometric view of the embodiment of the nulling optical bridge of FIG. 1 as assembled to a temperature active device.

An isometric view of a nulling optical bridge mounted to a temperature active apparatus (e.g., RF sputterer) is shown in FIG. 2. In this example, the change in temperature of a semiconductor wafer as a function of sputtering characteristics was intended to be measured.

In the FIG. 2, a laser 20 emits a beam which passes through a polarizer 22 and then is split into two beams (A and B) by a prism 24. Beam A is reflected from reflector 26 to detector 28. Beam B is directed toward a mirror 30 wherein the probe beam B is reflected to pass through a vacuum sealed window 32 of the sputterer. The probe beam B, then, passes through the holes (not shown) in the anode plate and base plate and is reflected at near normal incidence by the back side of a wafer 34 which covers the access hole in the sputterer. Upon exiting the sputter chamber, the probe beam is directed into the split detector 28 (e.g. a photodetector bi-cell) which measures its power relative to that of the reference beam.

The reflected power ($P_r$) at fixed incident wavelength is given by $$P_r = R \cdot P_i$$

where $P_i$ is the incidence power. A small change $\Delta R$ in sample reflectivity causes a proportionately small change in reflected power $$\Delta P_r = \Delta R \cdot P_i$$

so that the fractional change in reflectivity is given by $$\frac{\Delta R}{R} = \frac{\Delta P_r}{P_r}$$

By substitution for $\Delta R$ from the Taylor series expression above, and by neglecting the term in $C_2$, an approximate expression for the fractional change in reflected power can be obtained as:

$$\frac{(A' - B')}{\frac{1}{2}(A' + B')} = \frac{\Delta P_r}{P_r} = \frac{C_1(T - T_o)}{R(T_o)}$$

This equation is valid to a high degree of approximation and shows that the change in reflected power and the change in the nulling condition ($\Delta\phi$) is linearly proportional to the change in sample temperature. As the temperature of a silicon wafer increases, its reflectivity increases and this, in turn, causes an increase in the power of the probe beam upon reflection. Changes in probe beam power are continuously measured by the monitor optical bridge and are related to wafer temperature through the parameter $C_1$, which is determined in a calibration measurement.

Calibration of the coefficient $C_1$ for a silicon wafer was performed in the following manner. A chromel-alumel thermocouple was cemented to the back of the wafer within about a half-inch of the probe beam. The wafer was then heated in vacuum with a tungsten lamp and a plot of the thermocouple temperature versus signal was plotted on an X-Y recorder as the wafer cooled. Calibration data can also be obtained digitally and stored on a computer. The calibration data is used to obtain the coefficient $C_1$ which is used to relate the signal $\Delta\phi$ to the change in wafer temperature during sputtering.

From calibration data taken on nominally doped silicon with oxide on the measurement surface, and using the above equation for fractional change in reflected power, a value $C_1 = 4.2 \pm 0.5 \times 10^{-5}$° C.$^{-1}$ at 6328Å is obtained which will be recognized by those skilled in the art as being in agreement with the published values of the same. As $SiO_2$ has no optical transition in the visible spectrum and at the same incident wavelength, the same value for $C_1$ is obtained and is used as a standard even for a silicon wafer with a thick, thermally grown oxide layer.

In contrast, silicon nitride does have an optical absorption band in the visible spectrum and its absorption spectrum depends on how the nitride layer is grown. The absorptivity of nitride films have been found to vary with temperature. In this event, wafers with a nitride layer on the measurement surface will show an apparent value for $C_1$ that can vary significantly from that of silicon, and calibration data for each of these wafers is essential. The temperature dependent effects of a nitride layer can be eliminated by using a nulling bridge which has a longer probe wavelength. Emission in the 8500Å range is available with AlGaAs heterojunction lasers which can be substituted for the helium-neon laser without loss of sensitivity in the measurement.

Figure 3:
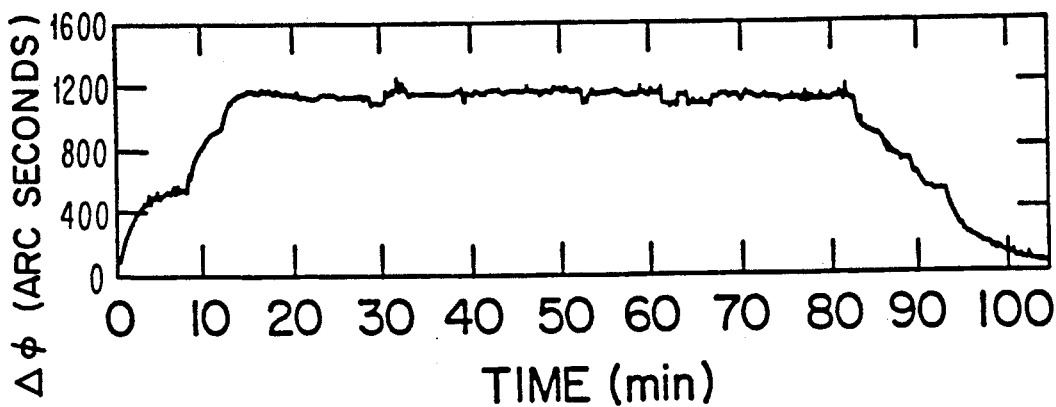
FIG. 3 is a plot of the temperature measurements made with the subject device on a sample silicon wafer.

FIG. 3 shows an example of the temperature measurements made with the subject device on a nominally doped silicon wafer sputtered with a thick oxide layer (greater than 1000Å) during sputtering. The x-axis shows the sputtering as a function of time. The y-axis shows the change in degrees (arc seconds) of the polarizer angle necessary to maintain the nulling condition between the split beams. From the graph it is readily seen that the RF power was increased to 5.4 kW in three steps and left undisturbed for 83 minutes when it was decreased to zero in four steps.

Figure 4:
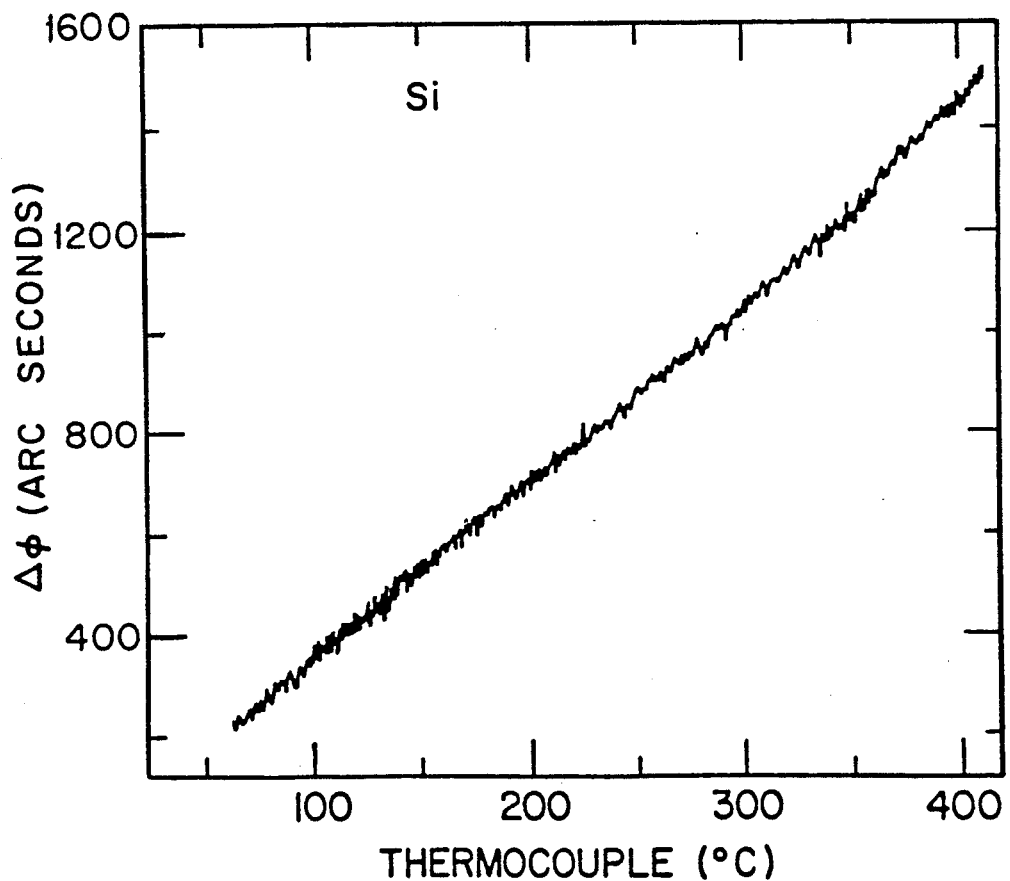
FIG. 4 is a plot of the change in polarization angle $\Delta\phi$ versus variation of silicon sample temperature as measured using a calibrated thermocouple.

The conversion from arc seconds from the y-axis in FIG. 3 to degrees C of temperature can be arrived at by using FIG. 4.

FIG. 4 represents the calibration data taken by the use of a thermocouple for the wafer of FIG. 3. The y-axis shows the change in polarizer angle $\Delta\phi$ necessary to maintain the null condition $(A' - B') = 0$. The x-axis is a function of temperature as measured by the thermocouple, described above, attached to the wafer. The slope $$\left(\frac{\Delta\phi}{\Delta T}\right)$$

of the curve gives the calibration parameter $\gamma$ which has the relative units of arc seconds /°C. and is subsequently used to convert the y-axis in FIG. 3 from arc seconds to °C.

In operation with a sputtering system, conversion to temperature from arc seconds/°C. requires the calibration step utilizing a thermocouple. With a sample such as silicon, the calibration can be recorded once and then applied to a variety of semiconductor devices of silicon or silicon with oxide coverage. However, in the presence of some sputtered materials, (e.g., a nitride layer), and at some optical wavelengths the calibration is not a very universal parameter because the absorbed power in the nitride layer and the temperature dependence of the absorbed power in the nitride layer both depend on the thickness of the nitride layer. Therefore, calibration would have to be made with each layer. However, by knowing the absorption spectrum of the nitride layer, a wavelength can be chosen so that the effects of the nitride are greatly minimized or eliminated from the temperature measurement of the silicon wafer of interest.

In an alternative embodiment, a double optical beam thermometer arrangement can be used to further minimize any measurement error due to such artifacts as mechanical motion of sample or gradual coating of vacuum windows, as during processing, through which the probe beam must pass to reach the sample. To minimize error in the presence of such artifacts, two nulling optical bridges can be used, one operating at a wavelength $\lambda_1$ at which the temperature dependence of the reflectivity is much smaller than that operating at a wavelength $\lambda_2$.

In operation, the two probe beams at the two different wavelengths follow the same path as described in FIG. 1 and are made to coincide by use of well known beam splitting techniques. The reflected optical probe beams are separated by well known beam splitting techniques and are incident on separate detectors. The two reference optical beams are also incident on separate detectors. As an example of the applicability of the two beam system, the temperature dependence of the reflectivity of silicon at a wavelength of 325 nm is well known to be much less than the temperature dependence of the reflectivity at visible and near infrared wavelengths. Therefore, observed changes at $\lambda_1 = 325$ nm can be subtracted from observed change at, say $\lambda_2 = 633$ nm, to obtain the desired temperature measurement as described in FIGS. 3 and 4.

While this invention has been described with respect to particular embodiments thereof, it will be apparent to those of skill in the art, that modifications may be made thereto without departing from the spirit and scope of the present invention.

Having thus described our invention, what we claim as new and desired to secure by Letters Patent is:

1. A nulling optical bridge for measuring the relative power of the two optical beams and the change in the reflection and/or transmissivity characteristics of a material under processing comprising:
   (a) illumination means for supplying a source of light,
   (b) adjustable polarizer means for linearly polarizing said source of light incident thereon,
   (c) prism means for splitting said light from said polarizer means into more than one beam,
   (d) first photodetector means,
   (e) reflection means for reflecting said beams from said prism means, with one of said beams being directed to be incident on the material under processing and another of said beams being reflected directed to said first photodetector means,
   (f) second photodetector means for receiving in synchronism said beam reflected from the material under processing, and
   (g) control means for comparing the power of said detected beam from the material under processing received by said second photodetector means to the power of said another beam received by said first photodetector means such that any differences in the relative power between these beams is fedback to adjust said polarizer means until the intensity of said beams is equalized.

2. An apparatus according to claim 1 wherein said illumination means is a coherent or incoherent source of light.

3. An apparatus according to claim 2 wherein said coherent source of light is a laser.

4. An apparatus according to claim 1 wherein said polarizer is adjustable by rotation of a stepper motor.

5. An apparatus according to claim 4 wherein each stepper motor incremental step is calibrated to correspond to a calibrated change in the reflection and/or transmissivity of the material under processing.

6. An apparatus according to claim 5 wherein said prism means splits said linearly polarized beam into two orthogonally polarized beams.

7. An apparatus according to claim 5 wherein the incremental steps of the stepper motor are calibrated as a function of temperature.

8. An apparatus according to claim 5 wherein the incremental steps of the stepper motor are calibrated as a function of ion implantation dose.

9. An apparatus according to claim 4 wherein said prism means comprises a polarization sensitive beamsplitter.

10. An apparatus according to claim 1 wherein said illumination means comprises first and second sources of light and said photodetector means comprises first and second photodetector means associatively operable in conjunction with said first and second sources of light respectively.

11. An apparatus according to claim 10 wherein said first and second sources of light are of different wavelengths.

* * * * *